United States Patent [19]

Besson et al.

[11] Patent Number: 5,801,286
[45] Date of Patent: Sep. 1, 1998

[54] PROCESS FOR THE PREPARATION OF A CATALYST FOR THE HYDROGENATION OF NITRILES TO AMINES AND USE OF THIS CATALYST IN HYDROGENATION

[75] Inventors: Michèle Besson, Les Echets; Georges Cordier, Francheville; Pierre Fouilloux, Caluire-et-Cuire; Jacqueline Masson, Eybens, all of France

[73] Assignee: Rhone-Poulenc Chimie, Courbevoie Cedex, France

[21] Appl. No.: 663,098

[22] PCT Filed: Dec. 16, 1994

[86] PCT No.: PCT/FR94/01477

§ 371 Date: Sep. 23, 1996

§ 102(e) Date: Sep. 23, 1996

[87] PCT Pub. No.: WO95/17960

PCT Pub. Date: Jul. 6, 1995

[30] Foreign Application Priority Data

Dec. 28, 1993 [FR] France .................. 93 16007

[51] Int. Cl.⁶ .................................. C07C 209/48
[52] U.S. Cl. .................... 564/490; 564/491; 564/492; 564/493; 502/301
[58] Field of Search .................... 564/490, 491, 564/492, 493; 502/301

[56] References Cited

U.S. PATENT DOCUMENTS

| | | | |
|---|---|---|---|
| 4,387,246 | 6/1983 | Disdier et al. | 564/417 |
| 4,429,159 | 1/1984 | Cutchens et al. | |
| 5,210,271 | 5/1993 | Mizuno et al. | 558/442 |
| 5,527,946 | 6/1996 | Flick et al. | 558/459 |

FOREIGN PATENT DOCUMENTS

| | | |
|---|---|---|
| 0 223 035 | 5/1987 | European Pat. Off. |
| 2 104 794 | 3/1983 | United Kingdom. |

OTHER PUBLICATIONS

Russian Chemical Reviews, Uspekhi Khimii, vol. 33, 1964.
Effect of Additives on the Activity of Hydrogenation Catalyst, (II), Yuzuru Takagi et al, vol. 55, No. 2, 1961.
Catalytic Hydrogenation of Raney Nickel Catalyst Modified by Chromium Hydroxide Deposition, T. Koscielski et al, Applied Catalysis, 49 (1989), pp. 91–99.

*Primary Examiner*—Brian M. Burn
*Attorney, Agent, or Firm*—Burns, Doane, Swecker & Mathis, L.L.P.

[57] ABSTRACT

The present invention relates to the field of the catalytic hydrogenation of nitriles to amines and, more particularly, of dinitriles such as adiponitrile (ADN) to diamines such as hexamethylenediamine (HMD).

More precisely, the present invention relates to a process for the preparation of a catalyst for the hydrogenation of nitriles to amines of Raney nickel type doped with at least one additional metal element selected from columns IVb, Vb and VIb of the periodic classification.

It is targeted at providing an economic and easy-to-implement process which makes it possible to obtain catalysts which are both active and selective with respect to nitriles and stable.

The process is characterized in that it consists in suspending Raney nickel in a solution, preferably an acid solution, of the additional metal element.

43 Claims, No Drawings

PROCESS FOR THE PREPARATION OF A CATALYST FOR THE HYDROGENATION OF NITRILES TO AMINES AND USE OF THIS CATALYST IN HYDROGENATION

The present invention relates to the field of the catalytic hydrogenation of nitrites to amines and, more particularly, of dinitriles such as adiponitrile (ADN) to diamines such as hexamethylenediamine (HMD) or to aminonitriles such as aminocapronitrile.

More precisely, the present invention relates to a process for the preparation of a catalyst for the hydrogenation of nitriles to amines of Raney nickel type doped with at least one additional metal element selected from columns IVb, Vb and VIb of the periodic classification.

It also relates to the catalysts obtained by implementation of this process and a final subject is an application of these catalysts in catalytic hydrogenation of nitriles to amines and, more precisely, but non-limitingly, of adiponitrile to hexamethylenediamine.

Catalytic hydrogenation has been carried out for a considerable time using Raney nickels, which are obtained by alkaline leaching of aluminium-rich Al/Ni precursor alloys, the leaching normally having the effect of causing the removal of most of the aluminium. The finished catalyst exists in the form of agglomerates of finely-divided nickel crystallites which are characterized by a high specific surface and a variable residual aluminium content.

Conventionally, the parameters which make it possible to assess the behaviour of a catalyst are the activity, the selectivity and the stability with time.

In an attempt to optimize these properties in Raney Ni hydrogenation catalysts, it has been proposed to add to them promoters or doping agents which are additional metal elements chosen from transition metals in the periodic classification (especially iron, cobalt, chromium, molybdenum, zirconium, tantalum or titanium).

According to a first, so-called "metallurgic" route, the doping or the incorporation of promoter in catalysts of Raney nickel type is carried out at the stage of the Ni/Al precursor alloy, before alkaline attack. Introduction of the doping agent into the alloy is carried out in the molten state.

The article by B. N. Tyutyunnikov, "The Soviet Chemical Industries, No. 6, June 1971, pages 380 to 382", as well as the written work by Freidling et al., "Russian Chemical Reviews, Vol. 33, No. 6, June 1964, pages 319 to 329", are prior bibliographic references which relate to Raney Ni catalysts doped with at least one transition metal by the metallurgic route. These known catalysts are not generally more satisfactory as regards activity, selectivity and stability with time. Thus, the catalysts disclosed in Tyutyunnikov et al. seem relatively specific for mononitriles derived from fatty acids containing 7 to 20 carbon atoms. However, this is not evidence of efficiency as regards, for example, dinitriles.

The Raney Ni catalysts doped and described by Freidling et al. are active on dinitriles but their selectivity with respect to the substrates remains low. Finally, the hydrogenation reaction conditions required for these catalysts (Ni/Al/Ti) are not ideal on an industrial scale: temperature of 140° to 180° C., hydrogen pressure of 140 bars and reaction medium consisting of n-butanol+ammonia.

Moreover, a second route for doping the hydrogenation catalyst of Raney nickel type is known, described especially by Takagi and Yamanaka in "Scientific Papers I.P.C.R. - Tokyo, 55 (1961), 105–108".

These writers propose to improve the activity and selectivity of catalysts of Raney nickel type by addition of various metal salts (copper, cobalt or chromium nitrates, ammonium molybdate, sodium tungstate or ferric chloride) during the stage of alkaline attack on the precursor alloy. The nitrile to be hydrogenated tested in these experiments is acetonitrile.

According to this document, the doped catalysts used would have an increased activity with respect to their non-doped homologues. These reports are questionable because they are made solely on the basis of visual observation of curves of the change in hydrogen consumption.

It should additionally be known that the incorporation of these metal salts in the alkaline leaching medium is capable of interfering with the process of preparing the catalyst.

T. Koscielski et al. have disclosed, for their part, in "Applied Catalysis, 49 (1989), 91–99, ESP BV", the doping of Raney Ni using solutions of $CrCl_3$ in alkaline medium (NaOH), so as to deposit finely-divided $Cr(OH)_3$ on the catalyst. The latter is active in the hydrogenation of cyclohexene, acetophenone and glucose. This teaching therefore does not apply to the hydrogenation of nitrites to amines. The Cr-doped catalysts described in this prior document are not, in fact, outstandingly effective in this type of hydrogenation.

In this state of the art, one of the essential objectives of the present invention is to provide a process for the preparation of doped catalysts of Raney Ni type for the catalytic hydrogenation of nitrites to amines and preferably of dinitriles to diamines or to aminonitriles.

Another objective of the invention is to provide a process for the preparation of such a catalyst which is convenient to implement and economic.

Another objective of the invention is to provide a process for the preparation of doped Raney Ni catalysts which are active, selective and stable in the context of the hydrogenation of nitrites to amines and preferably of dinitriles to diamines or to aminonitriles.

Another objective of the invention is to provide a hydrogenation process which makes use of these catalysts and which makes it possible in particular to achieve selectivities for hexamethylenediamine from adiponitrile which are greater than 95%.

To achieve these objectives, the Applicant company has had the credit of demonstrating, entirely surprisingly and unexpectedly, that the doping of Raney Ni with transition metal elements must advantageously be carried out on the finished catalyst using a solution of the said metal element.

The present invention thus relates to a process for the preparation of catalysts for the hydrogenation of nitrites to amines of Raney nickel type doped with at least one additional metal element selected from columns IVb, Vb and VIb of the periodic classification, characterized in that it consists in suspending Raney nickel in a solution, preferably an acid solution, of the additional metal element.

Such a process arrangement promotes the incorporation of the input metal element on the catalyst. Without wishing to be bound by theory, it seems, in fact, advantageous for the nickel to be slightly attacked by $H^+$ ions of the acid solution.

Within the meaning of the invention, the term acid corresponds to a solution whose pH is less than or equal to 7 and preferably greater than or equal to 0.5.

A pH of between 1 and 4 seems to be particularly appropriate.

In other words, the desirable acidity is that corresponding to a normality of between 0.3 and 0.5N.

This acidity can be introduced by the doping element as such, by a vehicle of this doping element or else alternatively by an acid-generating adjuvant and/or additional acid.

In accordance with the invention, it is preferable for the doping element or additional metal element used to be provided in the form of oxides or of salts, preferably inorganic acid salts or organic acid salts.

Inorganic acid salt denotes all conjugate ions of strong acids (such as, for example, HCl, H$_2$SO$_4$ or HNO$_3$) or of weak inorganic acids such as acid phosphates.

Mention may be made, as examples of organic acid salts, of: acetates, phthalates, adipates, citrates, tartrates or malonates.

The oxides also constitute support means for the doping agent, with a view to its incorporation in the Raney nickel catalyst. It can concern monoxides, dioxides, trioxides or others.

The chlorides, including especially TiCl$_3$, and the oxides are particularly preferred.

To complement or in place of the vehicle of the doping agent or of the doping agent itself, in order to provide the medium with acidity, it is possible, in accordance with the invention, to use an acid and/or acid-generating additive such as, for example, HCl, H$_2$SO$_4$, H$_3$PO$_4$, CH$_3$COOH, and the like. In this case, it concerns a simple acidity adjustment step which is entirely within the capacity of those skilled in the art.

It should be considered that the acid nature of the medium for the preparation of the doped Raney Ni catalyst corresponds to a preferred, but non-limiting, embodiment of the process according to the invention.

The adsorption of doping elements on the Ni/Al catalyst according to the above embodiments makes it possible to result in a particularly active Ni/Al/doping agent catalytic unit which is selective with respect to nitrites and, in particular, with respect to dinitriles such as adiponitrile.

This catalytic unit is also very stable with time and generates only very small amounts of hydrogenation impurities. This is particularly advantageous because, in certain cases, these impurities are very difficult to separate from the targeted amine. Mention may be made, as an example of such impurities, of diaminocyclohexane, a compound which has substantially the same boiling temperature as hexamethylenediamine resulting from the hydrogenation of adiponitrile.

According to another advantageous arrangement of the process according to the invention, the operation of placing in suspension is followed by a washing, preferably with water, of the Raney nickel at least partly doped with the additional metal element, at least one of these two operations optionally being repeated n times, n advantageously being between 1 and 5.

In order to perfect the doping of the Raney Ni catalyst suspended in the, preferably acid, solution of doping agent, it is therefore important to wash it well with water, the washing being repeated until the wash liquors are clear and neutral.

A number of successive operations of suspending the Raney Ni in the solution of doping agent can also be envisaged within the context of the process according to the invention.

The doped Raney catalyst obtained is collected after washing and is then stored, preferably, in a strong base such as, for example, NaOH, KOH or other alkali metal hydroxides.

In accordance with a variant of the invention, the Raney nickel, which is or is not doped, suspended in a solution of at least one additional metal element, is subjected to an alkaline leaching treatment carried out at a temperature greater than or equal to room temperature, preferably between 50° C. and 200° C. and, more preferentially still, between 80° C. and 120° C., this leaching optionally being carried out under a hydrogen pressure of between 0.1 and 20 MPa, preferably between 1 and 5 MPa and, more preferentially still, between 1.5 and 3 MPa.

In practice, this complementary treatment consists in placing the doped or non-doped catalyst in an alkali metal hydroxide solution (such as sodium hydroxide solution or the like) and in heating to approximately 100° C. with stirring and under a hydrogen pressure of approximately 2.5 MPa.

After this high-temperature alkaline attack, the catalyst is rinsed with alkali metal hydroxide solutions of decreasing assays and then with water until the wash liquors are neutral.

In the same way as above, storage of the Ni/Al/doping agent catalyst is carried out in a strong base such as sodium hydroxide solution or the like (1N).

Titanium is preferentially adopted as additional metal element. One of the corresponding appropriate vehicles is TiCl$_3$.

It appeared particularly advantageous to dope the Raney Ni catalyst until doping agent/Ni ratios of between 0.5% and 5%, preferably between 1% and 4% and, more preferentially still, between 1.2% and 3% by weight were obtained.

According to another embodiment of the process for the preparation of the catalyst in accordance with the invention, the incorporation of two doping elements of different nature, for example titanium and chromium, can be envisaged.

Another subject of the present invention is a process for the catalytic hydrogenation of nitrites to amines in which the doped Raney Ni catalyst obtained by the process of the invention described above is used.

By virtue of the catalyst resulting from the process according to the invention, the hydrogenation of nitrites to amines takes place particularly well and makes it possible to achieve entirely satisfactory activity and selectivity behaviour. Moreover, it is noted that the production of impurities remains limited.

The preparation of a doped Raney Ni catalyst and its application to the catalytic hydrogenation of nitrites to amines more particularly relate to dinitriles of formula (I):

$$NC-R-CN \qquad (I)$$

in which R represents a linear or branched alkylene or alkenylene group having from 1 to 12 carbon atoms or a substituted or unsubstituted arylene or aralkylene or aralkenylene group.

Use is preferably made in the process of the invention of dinitriles of formula (I) in which R represents a linear or branched alkylene radical having from 2 to 6 carbon atoms.

Mention may be made, as examples of such dinitriles, of especially adiponitrile, methylglutaronitrile, ethylsuccinonitrile, malononitrile, succinonitrile and glutaronitrile and their mixtures, especially the mixtures of adiponitrile and/or methylglutaronitrile and/or ethylsuccinonitrile which arise from the same process for the synthesis of adiponitrile.

In practice, the case where R=(CH$_2$)$_4$ represents an overwhelming opportunity because this corresponds to the conversion of ADN:

either to HMD, a diamine which constitutes one of the basic monomers in the manufacture of polyamide-6,6, or to aminocapronitrile, which makes it possible to obtain caprolactam, which is a precursor of polyamide-6.

Introduction of the nitrile substrate, for example adiponitrile, into the reaction medium is carried out while observing a concentration of between 0.001% and 30% by weight with respect to the total weight (w/w) of the reaction medium and preferably between 0.1% and 20% w/w.

The strong base used is preferably chosen from the following compounds: LiOH, NaOH, KOH, RbOH, CsOH and their mixtures.

In practice, use is preferentially made of NaOH and KOH, for a good compromise between performance and price, although RbOH and CsOH give even better results.

The hydrogenation reaction medium is preferably liquid. It contains at least one solvent capable of dissolving the nitrile substrate to be hydrogenated, it being known that this conversion takes place more readily when the said substrate is in solution.

According to an advantageous embodiment of the process according to the invention, use is made of an at least partially aqueous liquid reaction medium. Water is generally present in an amount less than or equal to 50%, advantageously less than or equal to 20%, by weight with respect to the total reaction medium. More preferentially still, the water content of the reaction medium is between 0.1 and 15% by weight with respect to all the constituents of the said medium.

To complement or substitute for the water, it is possible to provide at least one other solvent, of alcohol and/or amide type. Alcohols which are more particularly suitable are, for example, methanol, ethanol, propanol, isopropanol, butanol, glycols, such as ethylene and/or propylene glycol, polyols and/or mixtures of the said compounds.

In the case where the solvent consists of an amide, it can be, for example, dimethylformamide or dimethylacetamide.

When it is used with water, the solvent, which is preferably alcoholic, represents from two to four parts by weight per one part by weight of water and preferably three parts per one part of water.

According to another preferred characteristic of the invention, the amine whose preparation is targeted by the process is incorporated in the reaction medium. It is, for example, hexamethylenediamine when the nitrile substrate is adiponitrile.

The concentration of the targeted amine in the reaction medium is advantageously between 50% and 99% by weight with respect to all the solvent included in the said reaction medium and, more preferentially still, is between 60% and 99% by weight.

The amount of base in the reaction medium varies according to the nature of the reaction medium.

When the reaction medium contains only water and the targeted amine as liquid solvent medium, the amount of base is advantageously greater than or equal to 0.1 mol/kg of catalyst, preferably between 0.1 and 2 mol/kg of catalyst and more preferentially still between 0.5 and 1.5 mol/kg of catalyst.

In the case where the reaction medium comprises water and an alcohol and/or an amide, the amount of base is greater than or equal to 0.05 mol/kg of catalyst, is preferably between 0.1 and 10.0 mol/kg and more preferentially still between 1.0 and 8.0 mol/kg.

Once the composition of the reaction medium and the choice of the catalyst have been decided on, these two components are mixed and this mixture is then heated at a reaction temperature less than or equal to 150° C., preferably less than or equal to 120° C. and, more preferentially still, less than or equal to 100° C.

In concrete terms, this temperature is between room temperature (approximately 20° C.) and 100° C.

Prior to, simultaneously with or subsequent to the heating, the reaction chamber is brought to the appropriate hydrogen pressure, that is to say, in practice, between 0.10 and 10 MPa.

The duration of the reaction is variable according to the reaction conditions and the catalyst.

In a non-continuous operating mode, it can vary from a few minutes to a number of hours.

In a continuous operating mode, which it is entirely possible to envisage for the process according to the invention, the duration is obviously not a parameter which can be set.

It should be noted that a person skilled in the art can adjust the chronology of the stages of the process according to the invention, according to the operating conditions. The order given above only corresponds to a preferred, but non-limiting, form of the process according to the invention.

The other conditions which govern the hydrogenation (in continuous or non-continuous mode) in accordance with the invention involve technical arrangements which are conventional and known in themselves.

The examples which follow of the preparation of doped Raney Ni catalysts and of the hydrogenation of ADN to HMD will make it possible to understand the invention better. All the advantages of the invention and some of its variants will also emerge from the examples.

EXAMPLES

Example 1

Preparation of an Ni/Al/Ti catalyst, hereinafter denoted by the reference A

A purple solution containing 1.8% of $TiCl_3$ in 1.2% HCl is prepared in a 25 ml volumetric flask filled with argon.

Approximately 5 g of non-doped Raney Ni, obtained conventionally by leaching a commercial 50/50 by weight Ni/Al precursor alloy with sodium hydroxide solution, are withdrawn. They are rinsed with 20 ml portions of water until the wash liquors are neutral. 3.44 g of this wet catalyst are weighed in a pycnometer and are placed in a 100 ml round-bottomed flask. The round-bottomed flask is purged with argon. 20 ml of the $TiCl_3$ solution are then introduced onto the catalyst. The reaction medium is placed under a stream of argon and stirred for 1 hour. The solution very quickly becomes green.

After 1 hour, the catalyst A is washed with water until the wash liquors are clear and neutral. This catalyst A, thus doped with titanium, is stored in 1N sodium hydroxide solution.

The catalyst A has a Ti/Ni ratio by weight of 1.6%.

Example 2

Hydrogenation of adiponitrile (ADN) to hexamethylenediamine (HMD) with the catalyst A The catalyst A of Example 1 is withdrawn and washed 4 times with approximately 20 ml of water (until the wash liquors are neutral). Approximately 0.4 g of this catalyst is weighed precisely in a pycnometer.

6 g of adiponitrile are introduced, using a syringe, into a dropping funnel connected to an autoclave via a leakproof pipe. The dropping funnel is closed, purged and a hydrogen pressure of 2.5 MPa is established.

525 µl of 2N sodium hydroxide solution, 1475 µl of water and, after having filled the autoclave with argon, 40 g of solvent consisting of HMD, ethanol (EtOH) and water (63/31.5/5.5 by weight respectively) are placed in the autoclave equipped with a stirrer system. The medium thus contains 0.1% by weight of NaOH with respect to the total mass of solvent.

0.4 g of catalyst is then introduced into the autoclave, which is then carefully closed and purged 2 times with nitrogen. 2.5 MPa of hydrogen are then introduced and heating is carried out to 80° C. After having reached this temperature, stirring is begun and the adiponitrile contained in the dropping funnel is run into the autoclave. The end of the reaction is detected by the stabilization in the hydrogen consumption.

The reaction lasts 47 minutes. Chromatographic analysis of the hydrogenate makes it possible to calculate the yield of the reaction.

The selectivity (S) for HMD as a percentage is given by the relationship: 100—sum of the selectivities of the by-products. In fact, as HMD is used in the reaction solvent, it cannot be directly quantitatively determined very precisely. On the other hand, it has been verified that the by-products, taken as a whole, are all identified.

The selectivities for each of the by-products are represented by the molar percentage of the by-product formed with respect to the converted ADN. In all the examples and comparative tests carried out, the degree of conversion of the ADN (as well as that of the intermediate aminocapronitrile) is 100%.

The selectivities are the following: HMD=97.18%; HMI (Hexamethyleneimine)=0.38%; DCH (Diaminocyclohexane)=0.04%; AMCPA (Aminomethylcyclopentylamine)=0.05%; NEtHMD (N-Ethylhexamethylenediamine)=0.07%; BHT (Bishexamethylenetriamine)=2.27%.

Example 3

Preparation of an Ni/Al/Ti catalyst, hereinafter denoted by the reference $A_1$

Part of the catalyst A of Example 1 is withdrawn and placed with 30 ml of 6N sodium hydroxide solution in a 150 ml reactor. The medium is heated at 100° C. under 2.5 MPa of hydrogen with stirring for 1 hour.

The catalyst $A_1$ obtained is then rinsed with 10 ml of 3N, 2N and 1N sodium hydroxide solution and 3 times with 10 ml of water until the wash liquors are neutral. It is then stored in 1N sodium hydroxide solution.

Example 4

Hydrogenation of ADN to HMD with $A_1$

The catalyst $A_1$ of Example 3 is used as in Example 2. The reaction lasts 23 minutes. Chromatographic analysis of the hydrogenate makes it possible to calculate the following selectivities: HMD=96.81%; HMI=0.28%; DCH=0.33%; AMCPA=0.05%; NEtHMD=0.05%; BHT=2.04%.

Example 5

Preparation of an Ni/Al/Cr catalyst, hereinafter denoted by the reference B.

2.22 g of $CrCl_3$ are weighed in a 25 ml volumetric flask and the volume is made up to 25 ml with water.

5 g of non-doped Raney Ni of Example 1 are placed with 10 ml of water and 10 ml of $CrCl_3$ solution in a round-bottomed flask. The medium is stirred for 75 min. The catalyst B is then washed with water and then again placed in the round-bottomed flask in 10 ml of water and 10 ml of the $CrCl_3$ solution for 75 min. Finally, the catalyst B is recovered and washed to neutrality with 6 times 50 ml of water and stored in 1N sodium hydroxide solution.

The catalyst B has a Cr/Ni ratio by weight of 3.5%.

Part of this catalyst B is withdrawn, placed in 30 ml of 6N sodium hydroxide solution in a 150 ml reactor and is then heated at 100° C. with stirring and under 2.5 MPa of hydrogen for 1 hour. The catalyst $B_1$, thus treated, is recovered and rinsed with 10 ml of 3N sodium hydroxide solution, then of 2N sodium hydroxide solution, then of N sodium hydroxide solution and finally with 3 times 10 ml of water until the wash liquors are neutral. It is then stored in N sodium hydroxide solution.

Example 6

Hydrogenation of ADN to HMD with $B_1$

The catalyst $B_1$ of Example 5 is used as in Example 2. The reaction lasts 56 minutes. Chromatographic analysis of the hydrogenate makes it possible to calculate the following selectivities: HMD=95.24%; HMI=0.66%; DCH=0.05%; AMCPA=0.03%; NEtHMD=0.08%; BHT=2.24%.

Example 7

Preparation of an Ni/Al/Cr catalyst, hereinafter denoted by the reference C 0.85 g of $CrO_3$ are weighed in a 25 ml volumetric flask and the volume is made up to 25 ml with water. An orange $CrO_3$ solution is obtained with a concentration of 0.34 mol.l$^{-1}$.

5 g of non-doped Raney Ni of Example 1 are placed in 10 ml of water and 10 ml of the $CrO_3$ solution in a round-bottomed flask. The medium is stirred for 75 min. The catalyst is then washed with water and then again placed in the round-bottomed flask in 10 ml of water and 10 ml of the $CrO_3$ solution for 75 min. The catalyst C, thus treated two times with the chromium trioxide solution, is now transferred with 30 ml of 6N sodium hydroxide solution into a reactor and heated at 100° C. with stirring and under 2.5 MPa of hydrogen for 1 hour. It is recovered, rinsed with 10 ml of 3N sodium hydroxide solution, then of 2N sodium hydroxide solution, then of N sodium hydroxide solution and finally with 3 times 10 ml of water. It is then stored in N sodium hydroxide solution.

The catalyst C has a Cr/Ni ratio by weight of 2.1%.

Example 8

Hydrogenation of ADN to HMD with C

The catalyst C of Example 7 is used as in Example 2. The reaction lasts 1 hour 50 minutes. Chromatographic analysis of the hydrogenate makes it possible to calculate the following selectivities: HMD=96.13%; HMI=1.05%; DCH=0.09%; AMCPA=0.03%; NEtEMD=0.05%; BHT=1.79%.

Example 9

Preparation of an Ni/Al/Cr catalyst, hereinafter denoted by the reference D 2.15 g of non-doped Raney Ni of Example 1 are placed in an autoclave with 3 ml of water, 4.5 ml of the $CrO_3$ solution prepared as in Example 7 and 30 ml of 6N sodium hydroxide solution. The entire mixture is heated at 100° C. under 2.5 MPa of hydrogen and with stirring for 1 hour. The catalyst D, thus doped, is then rinsed with 10 ml of 3N sodium hydroxide solution, then of 2N sodium hydroxide solution, then of N sodium hydroxide solution and finally 3 times 10 ml of water. It is stored in N sodium hydroxide solution.

The catalyst D has a Cr/Ni ratio by weight of 1.5%.

We claim:

1. A process for the preparation of a catalyst, said process comprising suspending a Raney nickel type catalyst in an acid solution containing at least one additional element selected from the group consisting of chromium and titanium to obtain a Raney nickel type doped catalyst.

2. The process according to claims 1, wherein the additional metal element used is provided in the oxide or inorganic acid salt or organic acid salt form.

3. The process according to claim 2, wherein the additional metal element is provided in the chloride and/or oxide form.

4. The process according to claim 3, wherein the additional metal element is in the form of TiCl$_3$.

5. The process according to claim 1, further comprising washing the Raney nickel at least partly doped catalyst from 1 to 5 times.

6. The process according to claim 5, wherein the washing is conducted with water.

7. The process according to claim 5, wherein the suspending of the Raney nickel catalyst with acid solution occurs from 1 to 5 times.

8. The process according to claim 1, wherein the doped Raney nickel catalyst is collected and stored.

9. The process according to claim 8, wherein the storage is in a strong base.

10. The process according to claim 1, wherein the Raney nickel, suspended in a solution of at least one additional metal element, is subjected to an alkaline leaching treatment carried out at a temperature greater than or equal to room temperature.

11. The process according to claim 10, wherein the temperature is between 50° C. and 200° C.

12. The process according to claim 11, wherein the temperature is between 80° C. and 120° C.

13. The process according to claim 10, wherein the treatment is conducted under a hydrogen pressure of between 0.1 and 20 MPa.

14. The process according to claim 13, wherein the pressure is between 1 and 5 MPa.

15. The process according to claim 14, wherein the pressure is between 1.5 and 3 MPa.

16. The process according to claim 10, wherein the amount of additional metal element used and the reaction conditions are selected so that the catalyst obtained has a doping agent/Ni ratio of between 0.5% and 5 % by weight.

17. The process according to claim 16, wherein the catalyst obtained has a doping agent/Ni ratio of between 1% and 4% by weight.

18. The process according to claim 17, wherein the catalyst obtained has a doping agent/Ni ratio of between 1.2% and 3% by weight.

19. A process for the catalytic hydrogenation of nitrites to amines, said process comprising suspending a Raney nickel type catalyst in an acid solution containing at least one additional element selected from the group consisting of chromium and titanium to obtain a Raney nickel type doped catalyst: and exposing the nitrile to the doped Raney nickel catalyst in a liquid reaction medium along with a base.

20. The process according to claim 19, wherein the nitrile has the formula (I):

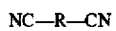
NC—R—CN            (I)

wherein R represents a linear or branched alkylene or alkenylene group having from 1 to 12 carbon atoms or a substituted or unsubstituted arylene or aralkylene or aralkenylene group.

21. The process according to claim 20, wherein R represents a linear or branched alkylene radical having between 2 to 6 carbon atoms.

22. The process according to claim 21, wherein the nitrile is selected from the group consisting of adiponitrile, methylglutaronitrile, ethylsuccinonitrile, malononitrile, succinonitrile, glutaronitrile or mixtures thereof.

23. The process according to claim 19, wherein the concentration of nitrile in the total reaction medium is between 0.001 % and 30% by weight.

24. The process according to claim 23, wherein the concentrate of nitrile in the total reaction medium is between 0.1% and 20% by weight.

25. The process according to claim 19, wherein the base is selected from the group consisting of LiOH, NaOH, KOH, RbOH and CsOH.

26. The process according to claim 19, wherein the liquid reaction medium comprises water.

27. The process according to claim 26, wherein the water is present in an amount of less than or equal to 20% by weight of the total liquid reaction medium.

28. The process according to claim 27, wherein the water is present in an amount of between 0.1% and 15 % by weight.

29. The process according to claim 19, wherein the liquid reaction medium contains targeted amine.

30. The process according to claim 28, wherein the targeted amine is introduced into the liquid reaction medium in a proportion of 50 to 99% by weight with respect to the weight of the total liquid reaction medium.

31. The process according to claim 30, wherein the targeted amine is introduced in a proportion of 60 to 99% by weight.

32. The process according to claim 19, wherein the liquid reaction medium comprises an alcohol and/or amide.

33. The process according to claim 32, wherein the alcohol is selected from the group consisting of methanol, ethanol, propanol, isopropanol, butanol, glycols, polyols and mixtures thereof, and the amide is selected from the group consisting of dimethylfomamide and dimethylacetamide.

34. The process according to claim 19, wherein the base is present in an amount greater than or equal to 0.1 mole/kg of catalyst.

35. The process according to claim 34, wherein the base is between 0.1 or 2.0 mole/kg of catalyst.

36. The process according to claim 35, wherein the base is between 0.5 and 1.5 mole/kg of catalyst.

37. The process according to claim 32, wherein the base is present in an amount greater than or equal to 0.05 mole/kg of catalyst.

38. The process according to claim 37, wherein the base is between 0.1 and 10.0 mole/kg of catalyst.

39. The process according to claim 38, wherein the base is present between 1.0 and 8.0 mole/kg of catalyst.

40. The process according to claim 32, wherein the hydrogeneration is carried out at a temperature of the reaction medium which is less than or equal to 150° C.

41. The process according to claim 40, wherein the temperature is less than or equal to 120° C.

42. The process according to claim 41, wherein the temperature is less than or equal to 100° C.

43. The process according to claim 33, wherein the alcohol is selected from the group consisting of ethylene glycol and propylene glycol.

* * * * *